United States Patent [19]

Weick

[11] Patent Number: 4,940,272
[45] Date of Patent: Jul. 10, 1990

[54] SUN VISOR FOR MOTOR VEHICLES

[76] Inventor: Heinz H. Weick, 94, rue de la Servette, 1202, Genf, Switzerland

[21] Appl. No.: 269,245
[22] PCT Filed: Feb. 2, 1988
[86] PCT No.: PCT/CH88/00024
§ 371 Date: Oct. 4, 1988
§ 102(e) Date: Oct. 4, 1988
[87] PCT Pub. No.: WO88/05731
PCT Pub. Date: Aug. 11, 1988

[30] Foreign Application Priority Data

Feb. 5, 1987 [CH] Switzerland ............... 406/87

[51] Int. Cl.$^5$ ............................................. B60J 3/00
[52] U.S. Cl. ..................... 296/97.5; 239/54; 239/56; 239/59; 239/289
[58] Field of Search .................... 296/97.5; 239/289 X, 239/53, 54 X, 56 X, 59 X, 58 X

[56] References Cited

U.S. PATENT DOCUMENTS

| | | | |
|---|---|---|---|
| 3,375,364 | 3/1968 | Marcus | 296/97.5 |
| 4,275,916 | 6/1981 | Skogler | 296/97.5 |
| 4,411,467 | 10/1983 | Cziptschirsch | 296/97.5 |
| 4,683,522 | 7/1987 | Viertel et al. | 296/97.5 |

Primary Examiner—Robert R. Song
Attorney, Agent, or Firm—Fleit, Jacobson, Cohn, Price, Holman & Stern

[57] ABSTRACT

An evaporator (X) for active fluid is built in a sun visor (1) for motor vehicles. It is composed of a housing (3,4) in which is rotatably and exchangeably mounted a hollow cylinder (5) provided with evaporation slots (5a). When the hollow cylinder (5) is manually turned, the slots (5a) move to a greater or smaller extent into the housing frame (4), thus regulating the desired degree of evaporation. The active fluid is contained in exchangeable cartridges (8) slid into the terminal section of the hollow cylinder (5) and filled with pads (9), and is transported by evaporation wicks (11) out of the cartridges (8) into the evaporation area (5b).

19 Claims, 2 Drawing Sheets

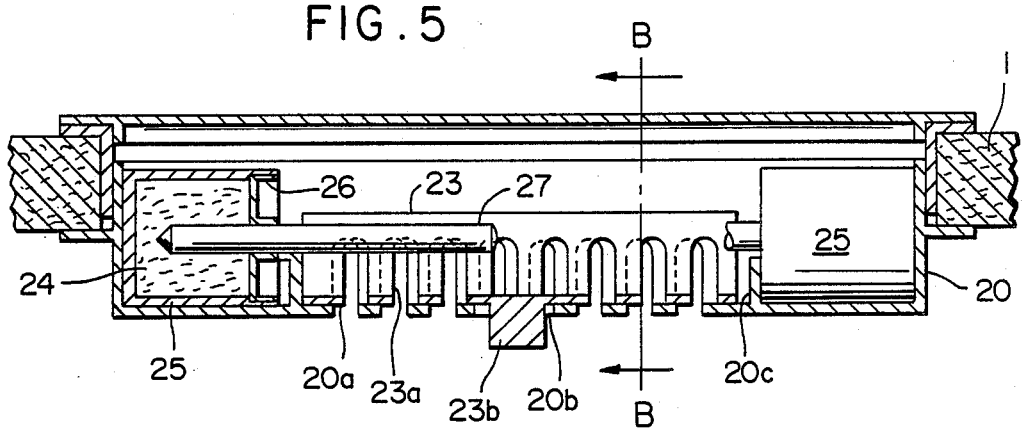
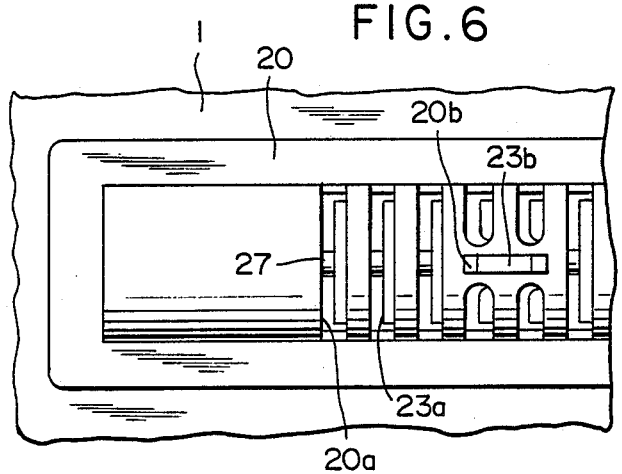
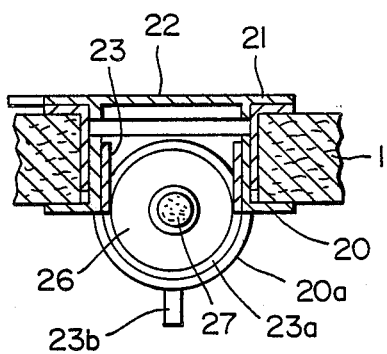
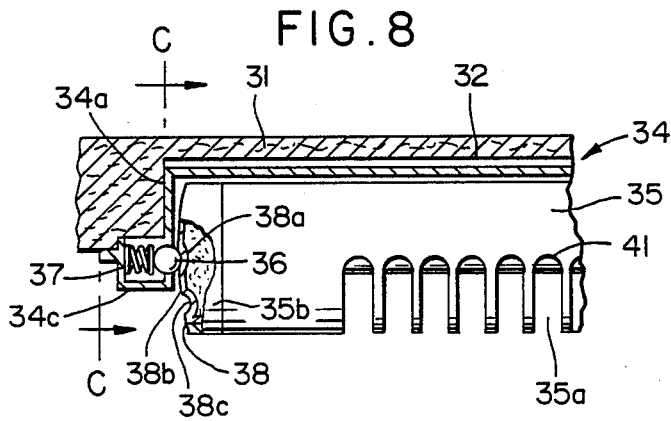
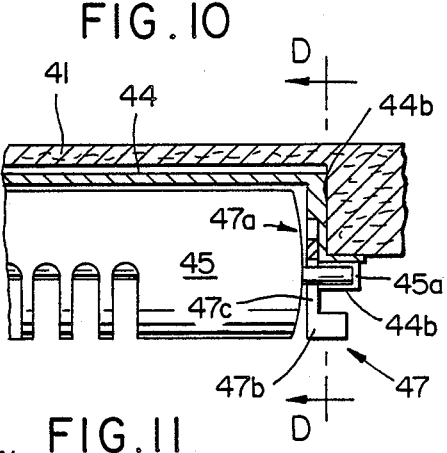
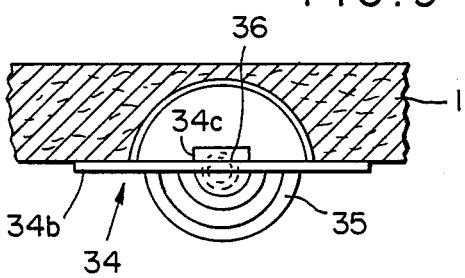
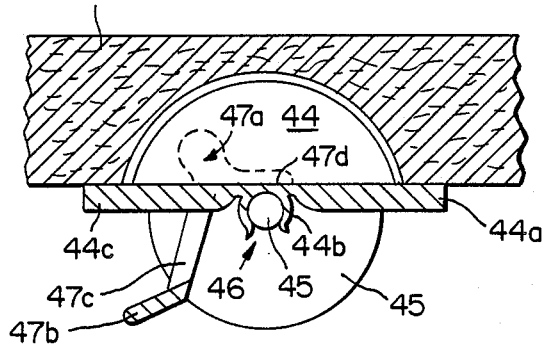

SUN VISOR FOR MOTOR VEHICLES

This invention concerns a sun visor for motor vehicles.

All motor vehicles today are equipped with such sun visors. It is also known that devices can be provided in the interior of the vehicle for evaporation of liquid agents to influence the interior air. These are used to deodorize the interior air or enrich it with perfumes or active agents that improve well-being or have a medicinal effect such as eucalyptus oil for inflammatory diseases of the respiratory tract. The evaporation results are especially good when the devices are placed in the path of the air flow of the interior circulation, which is the case when placed above an air outlet grid on the dashboard. In addition, an evaporation device is also known which can be mounted by means of suction cups on the interior of the windshield where they are then in the path of the air stream directed against it.

There are a variety of disadvantages to this implementation. An evaporative device mounted directly above an air outlet grid greatly decelerates the flow of air and evaporates too rapidly so the release of active agent is initially too great and then decreases very rapidly to a minimum. An evaporative device attached to the windshield is exposed to especially intense sunlight which in turn results in excessive evaporation. In each case the devices constitute a foreign body which projects more or less from the windshield and can be detached or shifted by an inadvertent brusque movement and rarely fits well with the design of the motor vehicle interior.

This invention is based on the problem of eliminating all these shortcomings in the simplest possible way.

This invention consists of the fact that the visor has a hollow space that is open on at least one side so the evaporative device can be inserted into it and at least partially recessed. The visor and evaporative device are thus combined to one component.

In this way the evaporative device is accommodated discretely and is also protected against harmful sunlight exposure. It is still in the path of the air circulation in front of the windshield, but the air flow is not so strong in the area of the sun visor that it can cause excessively rapid evaporation. From the sun visor the air stream is pointed directly at the driver or passenger so these persons are directly affected by the air enriched with the active agent, which is especially advantageous in the case of active agents with a medicinal or curative effect. The housing of the evaporative device is thus built into the sun visor panel in manufacturing the sun visor so assembly cost is very low.

The figures show practical examples of this invention, namely:

FIG. 5 shows one variation in longitudinal section.

FIG. 6 shows the lower view according to FIG. 5.

FIG. 7 shows cross section B—B according to FIG. 5.

FIG. 8 shows a longitudinal section of a lengthwise half of an evaporation device with an alternative rotating mount.

FIG. 9 shows the cross section C—C according to FIG. 8.

FIG. 10 shows the longitudinal half of the device that is the complement to FIG. 8 but equipped with a different rotating mount.

FIG. 11 shows the cross section D—D according to FIG. 10 on an enlarged scale.

Figure 1:
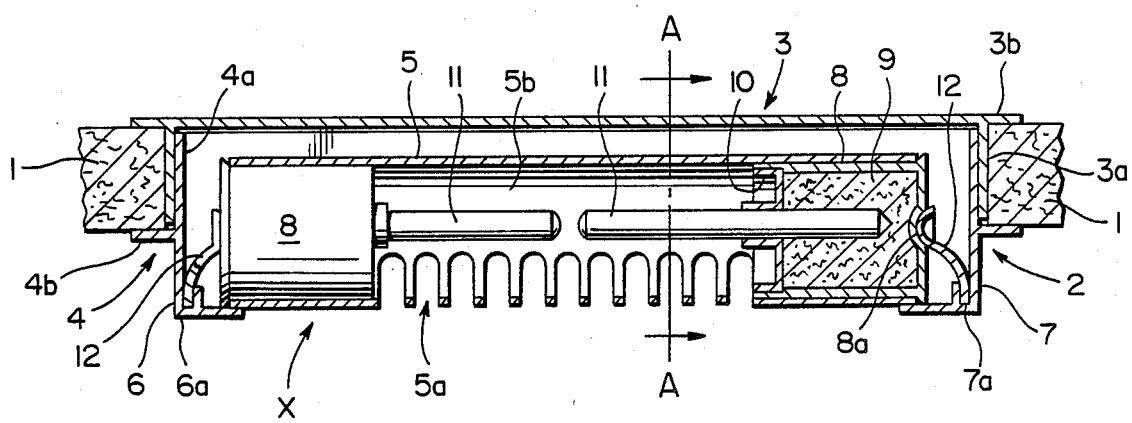
FIG. 1 shows a longitudinal section of an evaporative device built into a sun visor.
Figure 2:
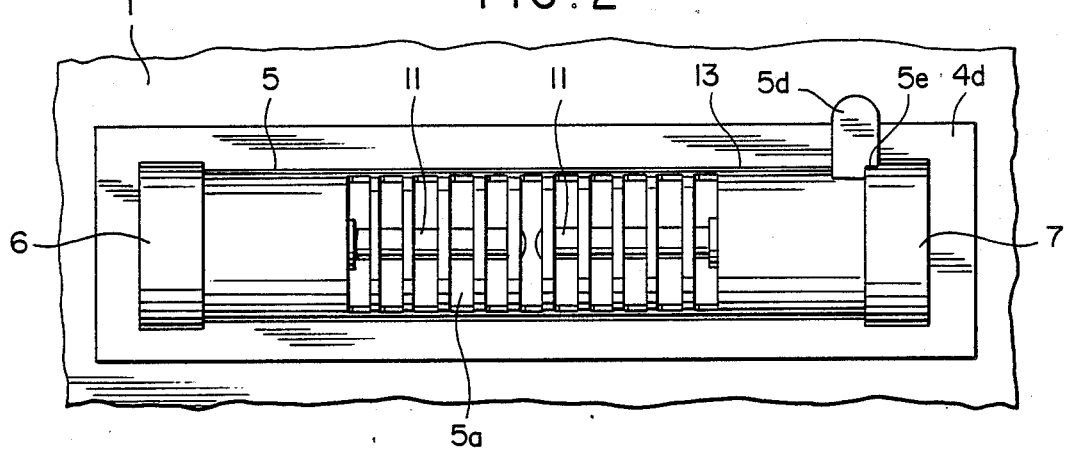
FIG. 2 shows a lower view of the device.
Figure 3:
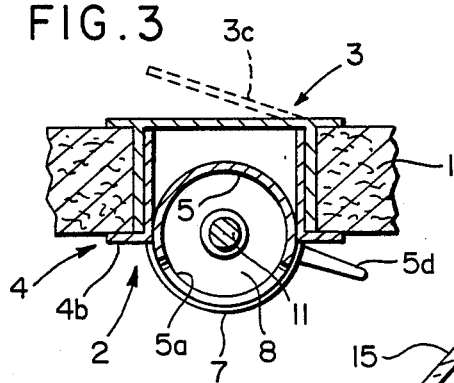
FIG. 3 shows a cross section A—A according to FIG. 1.

In accordance with FIGS. 1 to 3, the sun visor 1 of the sun visor is provided with a lengthwise opening 2 which holds the housing for the device consisting of shell-shaped part 3 inserted from one side and frame-shaped part 4 inserted from the other side. These parts extend with their side walls 3a and 4a into opening 2 and with their peripheral edges 3b and 4b they cover the peripheral areas of the opening. The mutual mounting of the peripheral walls 3a, 4a can take place by means of a mutual locking or screw connection (not shown) which should be designed in such a way that the housing can be inserted into visors of different thicknesses. The housing 3, 4 contains the hollow cylinder 5 which is somewhat shorter by comparison. Its two end areas are held by two semicircular mounting shells 6, 7 that are curved outward and are molded onto housing frame 4. Hollow cylinder 5 thus projects out of opening 2 with a cross-sectional area of about 180°. Hollow cylinder 5 is provided with transverse slits 5a in its middle longitudinal area. These also have an angular length of about 180°. Cartridge-like shells 8 containing pads 9 filled with the active agent are inserted into the end areas of hollow cylinder 5. The cartridges 8 are sealed by covers 10 through which linear wicks 11 which serve as the elements for evaporation project out of the pads into the evaporation space 5b of hollow cylinder 5. The two plate springs 12 which are mounted in grooves 6a, 7a of mounting shells 6, 7 and with their curved free end areas engage central conical recesses 8a of the cartridge bottoms are used to secure the position of hollow cylinder 5 and center it. A lever 5d molded onto the exterior of hollow cylinder 5 in radial direction is provided for operation, i.e., for manually turning hollow cylinder 5. It is provided with a short transverse groove 5e in its base area so the inner edge of mounting shell 7 projects into it. In the lever position or the rotational position of hollow cylinder 5 illustrated in FIGS. 2 and 3, the transverse slits 5 are completely inside frame opening 13. This yields the maximum evaporation effect. When lever 5d is pivoted to the other side, the transverse slits 5a in housing 3, 4 are covered so evaporation is suppressed. Between these two end positions, any intermediate positions are possible in accordance with the desired intensity of evaporation. The active agent is slowly and uniformly withdrawn from pads 9 by wicks 11, thus assuring a relatively homogeneous long-term effect. Once the active agent is consumed, all the empty cartridges 8 including wick 11 are changed, which is done by the following method. Hollow cylinder 5 is shifted to the left by lever 5d in axial direction, then tilted down and next pulled out of housing 3, 4 toward the right. Cartridges 8 can then be removed easily from hollow cylinder 5 and replaced by new ones. Then hollow cylinder 5 is inserted back into housing 3, 4 with the opposite sequence of manipulations. Due to the symmetry in the design, this can be done either from the right side or from the left side.

Since replacement units 8, 11 must be supplied in a gastight packaging, it is likewise possible, and even more practical for the consumer, for hollow cylinder 5 to be replaced at the same time, i.e., for the replacement unit to include hollow cylinder 5 and the cartridges 8 and wick 11 inserted into it. The airtight package of this exchange unit would then consist of a thin plastic sleeve sealed by a cover.

It is of course also conceivable for housing 3, 4 to be equipped only with the left spring 12, because hollow cylinder 5 is secured in transverse direction on the right side by lever 5d which extends somewhat beyond mounting shell 7, and this lever also serves as a stop.

If the most uniform possible long-term effect were to be omitted, then instead of the two cartridges 8 in hollow cylinder 5, simply one long pad filled with active agent could be placed in hollow cylinder 5 and would be centered by means of thin radial ribs. Likewise, an evaporating solid could be used as an active agent carrier in a known way.

Although the optimum equipment for the device would include two cartridges 8 of active agent, its functionality would naturally still be maintained even with only one cartridge. However, the evaporative output would then be lower. Furthermore, wick 11 should not be too long, because its capillary suction effect decreases with an increase in length.

If wick 11 were to pass through cartridge cover 10 at a lower point, i.e., eccentrically, then it would be shifted toward transverse slits 5a and would be affected even more intensely by the air stream for the purpose of achieving an even greater evaporative output. Instead of changing cartridges 8 or hollow cylinder 5 through housing opening 2, this manipulation would also be possible from the top side of the housing. To do so, the shell-shaped part 3 of the housing should be provided with an opening of a suitable size that could be closed by a cover 3c shown with dotted lines here. In this solution to the problem, lever 5b would have to be narrower so it could not reach beyond the inside edge of mounting dish 7.

Figure 4:
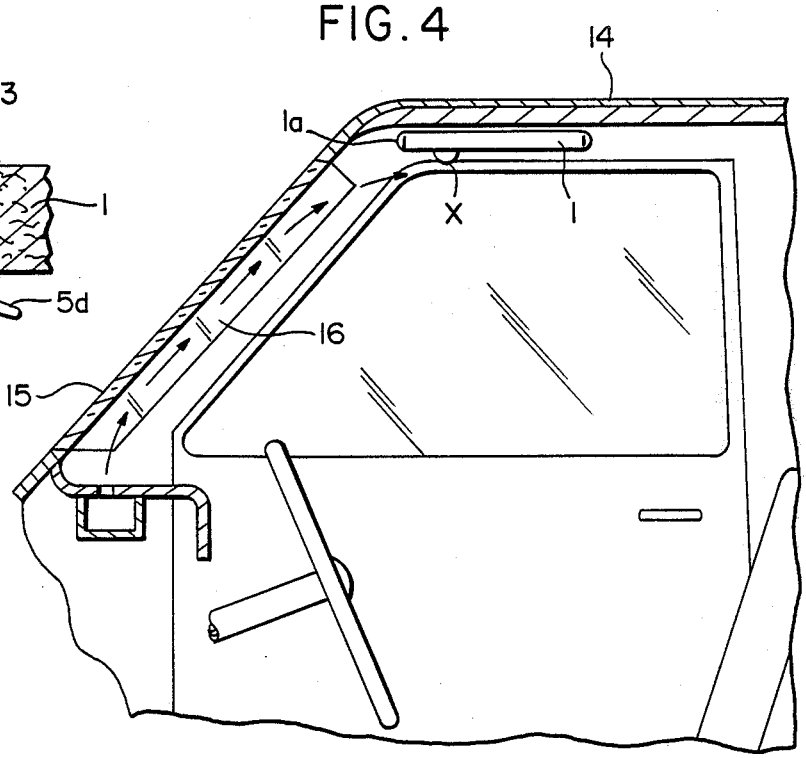
FIG. 4 shows a schematic diagram of the sun visor according to this invention in the assembled state.

FIG. 4 shows the sun visor according to this invention mounted in the interior of a motor vehicle. Sun visor 1 is mounted so it can pivot about axis of rotation 1a beneath motor vehicle roof 14. The evaporative device is labeled as X. The stream of air 16 rising at the front windshield 15 and diverted toward the rear at the top flows through the evaporative slits 5a which are concealed here and thus passes by wicks 11 and intensifies their evaporative effect. The air stream is aimed in the direction of the vehicle steering wheel from the evaporative device. For example, if an active agent is used to counteract fatigue, nervousness or inflammatory diseases of the respiratory tract, the high concentration of active agent in the stream of air striking the steering wheel will have an intense effect accordingly.

The evaporative device is protected against sunlight exposure and is secure, inconspicuous and elegantly positioned at a place where it will be disturbed by no one due to its installation in the sun visor.

In the version according to FIGS. 5 and 7, the housing of the device consists of housing shell 20 inserted into the sun visor panel 1, housing frame 21 inserted from above and housing cover 22 which seals it. Housing shell 20 projects with its semicircular bottom area out of sun visor panel 1 and is provided with transverse slits 20a that serve the function of evaporation. Within housing shell 20, there is a U-shaped slide 23 which is shorter in comparison with the housing shell and is provided with transverse slits 23a that coincide with respect to housing shell 20. The two middle transverse slits 20a and 23a are interrupted. At this point the housing shell 20 is provided with slit-shaped perforation 20b through which an operating piece 23b molded on slide 23 projects. This piece can move back and forth in longitudinal direction about the dimension of the width of slits 20a, 23a, and this movement is also executed by slide 23. In this way slits 20a, 23a can be made to coincide or they can also be pushed so far apart that they mutually close each other. In this way the evaporation from the device can be adjusted progressively from a maximum until it is completely suppressed. The active agent is in cartridges 25 which are filled with absorbent pads 24 through whose sealing cover 26 wicks 27 pass and which extend over transverse slits 20a, 23a. The cartridges 25 are accommodated in compartments that are open at the top and are formed by dividing walls 20c. To replace spent cartridges, housing cover 22 is opened and the cartridges are removed upward from housing shell 20 so new ones can be inserted.

Naturally a device of this design can be operated with only one cartridge.

If slide 23 were designed as a hollow cylinder, then cartridges 25 could be placed in the end areas.

Slits 20a, 23a could also run in the longitudinal direction of the device. Then, however, the movement of the slide could take place as a short rotational movement, i.e., in transverse direction, which would result in a uniform slit regulation.

It is also possible to eliminate cartridges 25 with this device, in which case a pad of a known type filled with active agent is simply placed in housing shell 20.

The evaporative device according to FIGS. 8 and 9 has a hollow cylinder 35 designed essentially according to the first practical example. The transverse slits are labeled as 35a and the active agent cartridges are 38 while the wicks here are labeled as 41. The housing 34 of the device is designed as a shell with a semicircular cross section and is inserted into the recess 32 of visor panel 31 which is closed at the top, and then its peripheral edge 34b reaches over the open area of recess 32.

In order to permit a rotating mount of hollow cylinder 35, housing shell 34 is provided with mounting compartments 34c that are open at one end and contain balls 36 that are under the influence of springs 37 (these mounting chambers 34 are located at the level of the peripheral edge 34b of the housing shell). Balls 36 pass through openings in the transverse walls 34a of the shell with one segment area and engage similarly shaped, centrally arranged mounting recesses 38a in the facing walls 38b of hollow cylinder 35, i.e., active agent cartridges 38, with a spring action.

This type of mount makes it possible to simply remove hollow cylinder 35 downward out of housing shell 34 without any prior axial movement for the purpose of replacing active agent cartridges 38. Then the cartridges can be replaced again in an equally simple manner. Removal is facilitated by annular grooves 38c (or a projecting circular edge) in facing walls 38 which provide the necessary fingertip grip. For the purpose of manual rotation, hollow cylinder 35 is provided with a knurl 35b on at least one end area.

The function of balls 36 can also be fulfilled by a pin with a curved end face and the function of helical spring 37 can also be fulfilled by a plate spring secured to transverse wall 34a, in which case the plate spring could be securely attached to the pin.

It is also possible for transverse wall 34a to have a cambered mounting projection shaped directly on it. Then the corresponding wall area is designed with a resilient effect accordingly. The type of practical dismantling and reassembly of hollow cylinder 5 in the manner described previously would not be affected by this measure.

For the sake of simplicity, this device can also be designed in such a way that cartridges 38 are together replaced with hollow cylinder 35 when in replacing the active agent.

The design according to FIGS. 10 and 11 differs from the practical example described previously only in the design of the mount of the hollow cylinder 45 which is provided here with mounting pins 45a. The mounts are shaped directly on the peripheral open edge 44a of housing shell 44. They are formed by circular resilient lamellae 44b between whose free ends, which are curved slightly outward, the plug openings 46 are located, so mounting pins 45a clip into the plug openings when hollow cylinder 45 is locked in place. Removal of hollow cylinder 45 is then simplified by a lever 47 that is operated in the manner of a push button. It is provided on the inside of facing wall 44b of housing shell 44 and is mounted on it so it can pivot about axis 47a. The longer lever arm 47c which is provided with the angled operating panel 47b projects through a recess 44c in the shell edge 44a while the shorter lever arm 47d acts from beneath against the corresponding mounting pins 45a. Thus by manual pressure on operating plate 47b, mounting pin 45a is pressed out of the mount so hollow cylinder 45 drops out of the housing shell 44.

It is sufficient to design only one of the two mounts in this way, while the other mount may be a simple plug-in hole.

The function of the molded spring action mounting tabs can also be fulfilled by an appropriately shaped plate spring which would then be accommodated in a molded mounting compartment. Housing shells 34 and 44 could then be glued into the hollow spaces of sun visor 31, 41.

If the hollow cylinder is included in the replacement unit, it can be left up to the purchaser of a new vehicle to fit the housing of the device with the hollow cylinder. Therefore it is proposed that the opening of the housing be manufactured so it is closed by a so-called blind cover and then the housing mounts for the hollow cylinder can be used to secure it.

Although all the devices described here are provided with means for regulating and closing the evaporative slits, sun visors with built-in evaporative devices that do not have any adjustment means would of course also fall within the scope of the present invention.

The practical examples illustrated and described here are of course only preferred designs which by no means exhaust the possibilities for implementation of this invention. In order to support this point, it should be pointed out again that the device may have a housing with a round cross-section mounted in a round hole in the visor at right angles to it. The area of this housing projecting out of the plane of the visor would be provided with slits on its circumferential wall. A pot-shaped rotating slide mounted in this housing area would also have slits molded on it to coincide with those in the circumferential wall. Then turning the rotating slide would take place by means of a central knob from the outside. Again the housing would be provided with a removable cover on the top for inserting and replacing the element containing the active agent.

I claim:

1. Sun visor for motor vehicles, said sun visor comprising
   a thick-walled visor panel provided with mounting devices for positioning said visor panel in the interior of a vehicle above the windshield so said visor panel can be pivoted from an initial horizontal position into an inclined functional position, said visor panel being provided with a hollow space open on at least one side and means for releasably mounting a device in the hollow space of said visor panel for evaporation of active agents for influencing the interior air in the vehicle.

2. Sun visor according to claim 1, wherein said means includes an elongated housing frame inserted into the hollow space of the visor panel with the device including a hollow cylinder containing the active agents and is provided with evaporative openings and having a circumferential zone with a partial circular shape in cross section, with end areas of the hollow cylinder being rotatably mounted in said housing frame, and the cylinder projecting beyond the housing frame as well as the visor panel with about 180° of its cross section.

3. Sun visor according to claim 2, wherein wall areas of said housing frame include semicircular mounting shells extending over the end areas of said hollow cylinder, and an operating lever projects approximately radially out of the housing frame and is molded onto a periphery of the housing frame.

4. Sun visor according to claim 2, wherein an interior space of the housing frame is longer in comparison with the hollow cylinder, and a spring element applies pressure in an axial direction to at least one of the facing sides of said hollow cylinder.

5. Sun visor according to claim 2, wherein at least one facing wall of the hollow cylinder is provided with a central mounting recess and at least one transverse wall of the housing frame has a mounting element under spring pressure in a longitudinal direction of the housing frame and engages in the central mounting recess of the hollow cylinder with a curved end area.

6. Sun visor according to claim 2, wherein at least one facing wall of the hollow cylinder is provided with a central mounting pin and at least one transverse wall of the housing frame has a mount to receive the central mounting pin so the mount can be spread apart with a spring action in the transverse direction of the frame and has a plug-in opening toward its plane of opening.

7. Sun visor according to claim 2, wherein said hollow cylinder has a chamber filled with an absorbent pad containing the active agents in at least one of its two end areas and a linear wick extending out of the chamber and into an evaporative space of the hollow cylinder.

8. Sun visor according to claim 7, wherein the chamber is surrounded by a cartridge-like sleeve inserted into one end area of the hollow cylinder so the linear wick passes through its inner facing wall.

9. Sun visor according to claim 2, wherein the housing frame is in the shape of a shell with a molded bottom.

10. Sun visor according to claim 2, wherein the hollow space of the visor panel is an opening into which the housing frame is inserted from one side while the other side of the opening is closed by a shell-like cover plate.

11. Sun visor according to claim 1, wherein the evaporative device has an elongated housing shell containing the active agents and is inserted with part of its side wall into the hollow space which is formed as an opening in the sun visor from one of two open sides, and an area of the shell projecting out of the opening is provided with parallel slits along part of its length, and a thin-walled slide that is next to an inside surface is provided in the projecting area of the shell and has a matching slit arrangement, and a molded operating piece passes through a guide slit of the projecting shell area and also through said means including a housing frame inserted from the other side into the opening and covered by a removable cover.

12. Sun visor according to claim 11, wherein said device includes a cartridge-like hollow body holding a pad the active agents is in at least one of two end areas of the housing shell, and an evaporative element designed as a linear wick extends out of the hollow body into the space above the slit arrangement.

13. Sun visor according to claim 12, wherein the slide is a hollow cylinder and has a chamber that holds the pad containing the active agents in at least one of its two end areas.

14. Sun visor according to claim 13, wherein said chamber is surrounded by a cartridge-like shell inserted into one end area of the hollow cylinder whose inner facing wall has the wick passing through it.

15. Sun visor according to claim 6, wherein a pivot lever is mounted on one of the transverse walls of the housing shell so the lever can be pivoted, and an extended lever arm projects outward past the housing shell and a shorter lever arm reaches beneath a mounting pin.

16. A fragrance evaporative device for mounting in the interior of an automobile, said device comprising:
a hollow cylinder having transverse slits with an angular length of 180°,
fragrance means mounted in said cylinder for release of fragrance through said slits,
a housing shell having an opening,
mounting means for rotatably mounting said cylinder in said opening of said housing shell so that said cylinder is rotatable to a first position where said slits are exposed to an air stream and a second position where said slits are enclosed by said housing shell to prevent exposure of said slits to the air stream, and
removal means for releasing said cylinder from said mounting means for replacement of said cylinder when all of the fragrance has been released from said fragrance means,
said housing shell including means for mounting said housing shell in the air stream on a surface of the interior of the automobile.

17. A fragrance evaporative device as claimed in claim 16, wherein said cylinder includes mounting pins located at opposite ends of said cylinder, said pins engaging said mounting means for rotatably mounting said cylinder in said housing shell.

18. A fragrance evaporative device as claimed in claim 17, where said mounting means includes curved resilient lamellae.

19. A fragrance evaporative device as claimed in claim 16, wherein said removal means includes a lever mounted on said housing shell for pivotal movement to force said cylinder from said mounting means.

* * * * *